(12) United States Patent
Jung

(10) Patent No.: US 9,101,502 B2
(45) Date of Patent: Aug. 11, 2015

(54) STENT COMPRISING TERMINAL ANCHORING ELEMENTS

(75) Inventor: Johannes Jung, Karlsruhe (DE)

(73) Assignee: PFM MEDICAL AG, Cologne (DE)

( * ) Notice: Subject to any disclaimer, the term of this patent is extended or adjusted under 35 U.S.C. 154(b) by 0 days.

(21) Appl. No.: 10/571,874

(22) PCT Filed: Sep. 16, 2004

(86) PCT No.: PCT/DE2004/002071
§ 371 (c)(1),
(2), (4) Date: Apr. 11, 2006

(87) PCT Pub. No.: WO2005/027789
PCT Pub. Date: Mar. 31, 2005

(65) Prior Publication Data
US 2007/0067016 A1 Mar. 22, 2007

(30) Foreign Application Priority Data
Sep. 16, 2003 (DE) .................................. 103 42 757

(51) Int. Cl.
*A61F 2/91* (2013.01)
*A61F 2/86* (2013.01)
*A61F 2/89* (2013.01)
*A61F 2/848* (2013.01)
*A61F 2/915* (2013.01)

(52) U.S. Cl.
CPC . *A61F 2/91* (2013.01); *A61F 2/848* (2013.01); *A61F 2/86* (2013.01); *A61F 2/89* (2013.01); *A61F 2/915* (2013.01); *A61F 2002/8486* (2013.01); *A61F 2002/91525* (2013.01); *A61F 2002/91533* (2013.01); *A61F 2002/91558* (2013.01); *A61F 2210/0019* (2013.01); *A61F 2220/0008* (2013.01); *A61F 2220/0016* (2013.01); *A61F 2230/005* (2013.01); *A61F2230/0054* (2013.01); *A61F 2230/0078* (2013.01); *A61F 2250/0037* (2013.01); *A61F 2250/0039* (2013.01); *A61F 2250/0098* (2013.01)

(58) Field of Classification Search
CPC ................ A61F 2/86; A61F 2/89; A61F 2/91; A61F 2/915; A61F 2/848; A61F 2002/8486; A61F 2002/821; A61F 2250/0098; A61F 2250/0069; A61F 2250/0039; A61F 2220/0008; A61F 2220/0016
USPC ............. 623/1.15, 1.16, 1.31, 1.34, 1.35, 1.3, 623/1.36
See application file for complete search history.

(56) References Cited

U.S. PATENT DOCUMENTS 5,593,442 A * 1/1997 Klein ............................ 623/1.16
6,270,524 B1 * 8/2001 Kim ............................. 623/1.15
(Continued)

*Primary Examiner* — David Isabella
*Assistant Examiner* — Suba Ganesan
(74) *Attorney, Agent, or Firm* — Grossman, Tucker, Perreault & Pfleger, PLLC

(57) ABSTRACT

The invention relates to a stent comprising terminal anchoring elements. Said stent (10) is provided with a tubular wall that extends along a longitudinal, flexible tubular axis (26), is formed from a flexible grid structure, and has tube ends (20) lying on opposing axis ends. Said wall consists of annular wall segments (11) that are lined up along the axis and are interconnected by means of connection segments (12). The annular wall segments (11) contain wall elements (14, 15) having an elastic structure. The inventive stent is characterized in that the wall comprises a flexible, arched anchoring element (22) on at least one tube end (20, 20'), said anchoring element being connected to at least two terminal wall elements (14, 15, 14', 15') in such a way as to form one component, bridging at least one elastic wall element (14, 15), and there is a larger radial distance between the ogive (24) of the arched anchoring element (22) and the tubular axis (26) than between the terminal wall elements (14, 15) and the tubular axis.

7 Claims, 4 Drawing Sheets

(56) References Cited

U.S. PATENT DOCUMENTS

| | | |
|---|---|---|
| 6,585,758 B1 * | 7/2003 | Chouinard et al. .......... 623/1.16 |
| 6,926,690 B2 * | 8/2005 | Renati .......................... 623/1.31 |
| 2001/0021872 A1 * | 9/2001 | Bailey et al. ................. 623/1.24 |
| 2001/0027339 A1 * | 10/2001 | Boatman et al. ............. 623/1.15 |
| 2002/0058988 A1 * | 5/2002 | Fischell et al. ............... 623/1.15 |
| 2002/0138135 A1 * | 9/2002 | Duerig et al. ................ 623/1.24 |
| 2002/0143386 A1 * | 10/2002 | Davila et al. ................. 623/1.15 |
| 2004/0098099 A1 * | 5/2004 | McCullagh et al. ......... 623/1.15 |

* cited by examiner

STENT COMPRISING TERMINAL ANCHORING ELEMENTS

The invention relates to a stent for insertion into tubular hollow organs, especially those of the human body.

Generic stents and their use are known in the art, and they are inserted into tubular hollow organs to expand and keep them open. These types of stents have a grid- or spiral-shaped structure consisting of wall segments. Between and within the wall segments, grid openings are formed that allow this structure to grow into the tissue at its implantation location. Such stents are known in the art and described, for example, in DE-A 197 46 88 or in WO 03/063 733.

There has already been an attempt to design stents so that they no longer change their position following installation. EP-A 0 778 011, for example, describes the design of thickened stent ends, wherein tissue from the vascular wall grows around the outwardly protruding, thickened ends following implantation, a technique intended to prevent a change in position, that is, a shift along the axis of the tubular structure. DE-A 197 46 882 describes a stent whose tubular grid structure consists of elastic wall segments that are designed elastically in a zigzag or V-shaped pattern and the sharp ends of which are expanded outward in a radial direction relative to the tubular axis, which is intended to prevent positional stability [sic], even in substantially curved blood vessels.

The goal of the invention is to provide a stent, especially an expandable stent, which not only guarantees positional stability, but can also be used in the region surrounding the heart, in particular, as well as in proximity to moved and/or substantially lateral bifurcations without the risk of obstructing the flow of blood to the bifurcation.

This goal is accomplished with the features defined in the claims.

It was found that the aforementioned goals can be accomplished by disposing curved anchoring elements that are linked integrally with the wall elements formed by the terminal wall segments on a stent of the generic type. In this regard, non-adjacent elements are preferably linked in a bridge-like manner. The anchoring element features, at the tip of its curve, a larger radial distance from the stent axis than the terminal wall elements, so that the end is expanded outward relative to the diameter or the lumen of the tubular stent, and the ends or tips of the curves are anchored in clamp- or claw-like fashion into the organ wall at the implantation location.

Both the anchoring elements and the wall segments are made of frames and are preferably wider and/or thicker than the frames of the wall elements. The shape of the curved anchoring elements can be both purely circular and oval or elongated oval. However, it is preferable for the curve to be formed as a V-shaped ogive. In an especially preferred embodiment, the ogive follows a slightly s-shaped curve. At the tip of the curve, the anchoring element is preferably thickened and, in an especially preferred embodiment, it is designed to be radiopaque in this region. In this manner, the treating physician can precisely follow the terminal points and position of the stent during surgery. The ends or feet of the curved or V-shaped anchoring element are integrally connected with the wall elements of the stent, and are neither welded, glued or connected to the stent by means of any other bonding technique.

In an especially preferred embodiment, the curve of the anchoring element bridges two non-adjacent wall elements of a terminal, annual wall segment. Normally at least one, but preferably two additional elements are disposed between the bridged wall elements. In the terminal region of the stent, unlike the middle segment, the wall segments are directly connected to one another without spring elements, so that they cannot expand or can only expand to a limited extent in the axial direction of the tube. In this manner, the terminal region of the stent, despite being flexible, is provided with the strength required and sufficient for anchoring.

The formation of the wall segments in the region between the stent ends can be designed in any manner in the embodiment according to the invention. Such flexible wall segments are known to the person skilled in the art and are described, for example, in DE-A 100 50 930, DE-A 197 46 882, and elsewhere.

The stent according to the invention is preferably made of elastic, annular wall segments, which are disposed along a longitudinal axis, thereby forming a tubular grid wall. As a result of its elasticity, the stent can conform to the movements of the hollow organ into which it is implanted. The individual wall segments are connected to one another by means of a continuous longitudinal frame. In a special embodiment, the longitudinal frame is designed to be continuously linear, thus enabling it to absorb compressive strain or tensile stress in a longitudinal direction without resulting in a longitudinal change in the stent. In the same manner, a contraction, that is, a pressing together of the individual wall segments, also does not result in a longitudinal change in the stent, because the tensile stress or compressive strain that may occur in this process is transferred to and absorbed by the continuous longitudinal frame.

A further embodiment of the invention is characterized by the fact that the annular wall segments comprise wall elements and/or are constructed from a plurality of such elements. These wall elements are preferably elastic elements that are alternately arranged in an angle relative to one another formed by first elastic elements and second elastic elements. This produces a zigzag elastic structure for the wall segments, so that an effective, elastic effect is achieved, which also allows for expansion in a radial direction relative to the stent axis and causes the supporting effect on the hollow organ.

The elastic elements can be formed to be approximately straight-lined. This straight-lined shape is to be considered as being relative to a projection onto an external circumference surface of the stent.

The connecting elements advantageously connect either only first or second elastic elements to one another. The connection elements themselves are not elastic relative to compressive and tensile forces acting along the stent longitudinal axis and are essentially rigid, i.e., said elements, together with the elastic elements they connect, absorb these tensile and compressive forces and prevent a longitudinal change in the stent. As a result, the connected first or second elastic elements, together with the connecting segments, form the continuous longitudinal frame. To this end, the connecting segments and the elastic elements connected to them should be arranged in parallel to one another. This applies, once again, relative to a projection onto a circumferential surface of the stent. In this manner, it is ensured that the applied force acts only along the longitudinal frame and has no lateral component that could lead to an unwanted shortening or lengthening of the stent. This precludes a non-linear course allowing for longitudinal expansion or contraction, as can occur, for example, as a result of a zigzag or wave-shaped course of the longitudinal frame.

An embodiment of the invention is characterized by multiple longitudinal frames that progress in parallel to one another in a projection onto an external circumferential surface, which are disposed to be spaced relative to one another in a circumferential direction. These can consist, for example, or three or four longitudinal frames. In this manner, the wall segments are positioned relative to one another in an especially effective manner, at the same time reliably avoiding a longitudinal change in the stent.

It is also possible for the longitudinal frame to have a helical shape. This can be the case, for example, when the longitudinal frame consists of the connecting segments and the first and/or second elastic elements. This results in an especially simple structure.

Nevertheless, longitudinal changes as a result of compression strain or tensile stress or compression of the stent are reliably avoided.

The connecting elements can also be thicker and/or wider than the elastic elements. Complexity is reduced, in particular, when a self-expanding stent is cut, by means of a laser, from a tubular object with a small diameter. In the first state, involving a small diameter, the connecting elements are formed, for example, to be approximately S-shaped. In the second state, involving a larger diameter, the connecting elements feature at least one component in parallel to the longitudinal frame. The connecting segments can, for example, be twice as wide as the elastic elements. This results in an especially straightforward pattern.

The stent is preferably designed to be made in one piece. This results in a stable design without unnecessary edges or predetermined breaking points. A shape memory material, such as a so-called memory metal, namely a nickel-titanium alloy, which is also marketed under the name Nitinol, can be used as the material for the stent. Polymers of the type used in other areas of medicine for implantation into the body are also suitable for production of the stent according to the invention. Using laser beams, for example, a suitable pattern for preparing the elastic elements and the connecting elements can be cut from a tubular material with a small diameter. The expanded shape can then be stamped onto the tubular object in a manner known in the art. If the stent produced in this manner is then compressed into a state in which it has a small diameter and, by means of a catheter, for example, is introduced into a diseased blood vessel, the stent, in its position, can once again be automatically returned to the stamped shape by heating via what is known as the conversion temperature.

Other possible materials for the stent include stainless steel, plastic or so-called self-dissolving materials. These self-dissolving materials, in particular, are advantageous when a stent is not intended to be installed permanently. If self-expanding stents are not used, they can be expanded in the desired position by means of a balloon catheter, for example.

Preferably, the surface of the stent should be processed, especially refined, smoothed and/or polished. This results in a smooth surface tolerated by the body.

The invention is described in greater detail on the basis of the following figures.

Figure 1:
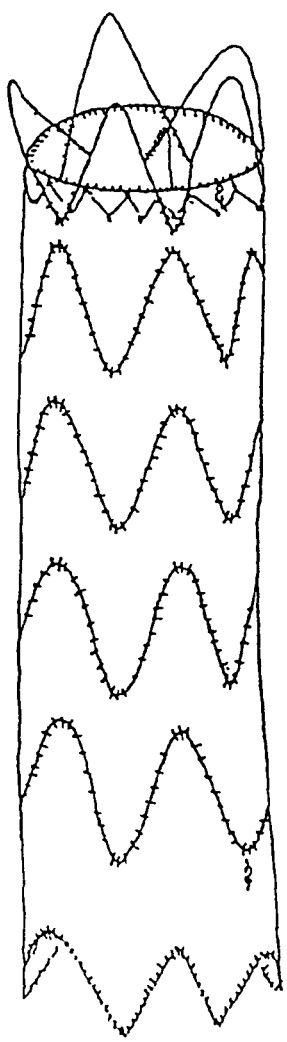
FIG. 1 shows a commercial stent according to the prior art.

In a stent according to the prior art, as shown in FIG. 1, sine wave-shaped wall segments are sewed onto a cylindrical, fabric-like material. The sine wave-shaped wall segments are only connected to one another as a frame at the seam of the cylindrical fabric. At its upper end, the stent features a sewed-open, open wire segment, which is formed in the same manner as the wave-shaped wall segments, but progresses in precisely the opposite direction, i.e., is shifted by a half phase without the open end segment touching the wall segments. For reinforcement purposes, the upper edge of the fabric material is reinforced with a wire thread progressing in a zigzag pattern.

Figure 2:
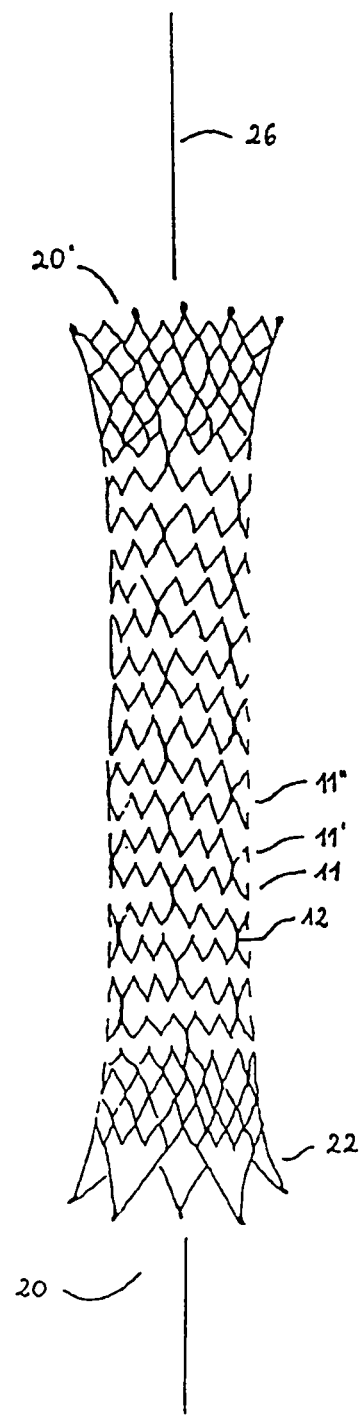
FIG. 2 shows a stent with anchoring elements according to the invention.

FIG. 2 shows a stent according to the invention whose grid-shaped tube wall is formed by means of a conventional pattern, as described, for example, in DE-A 197 46 882.

Figure 3:
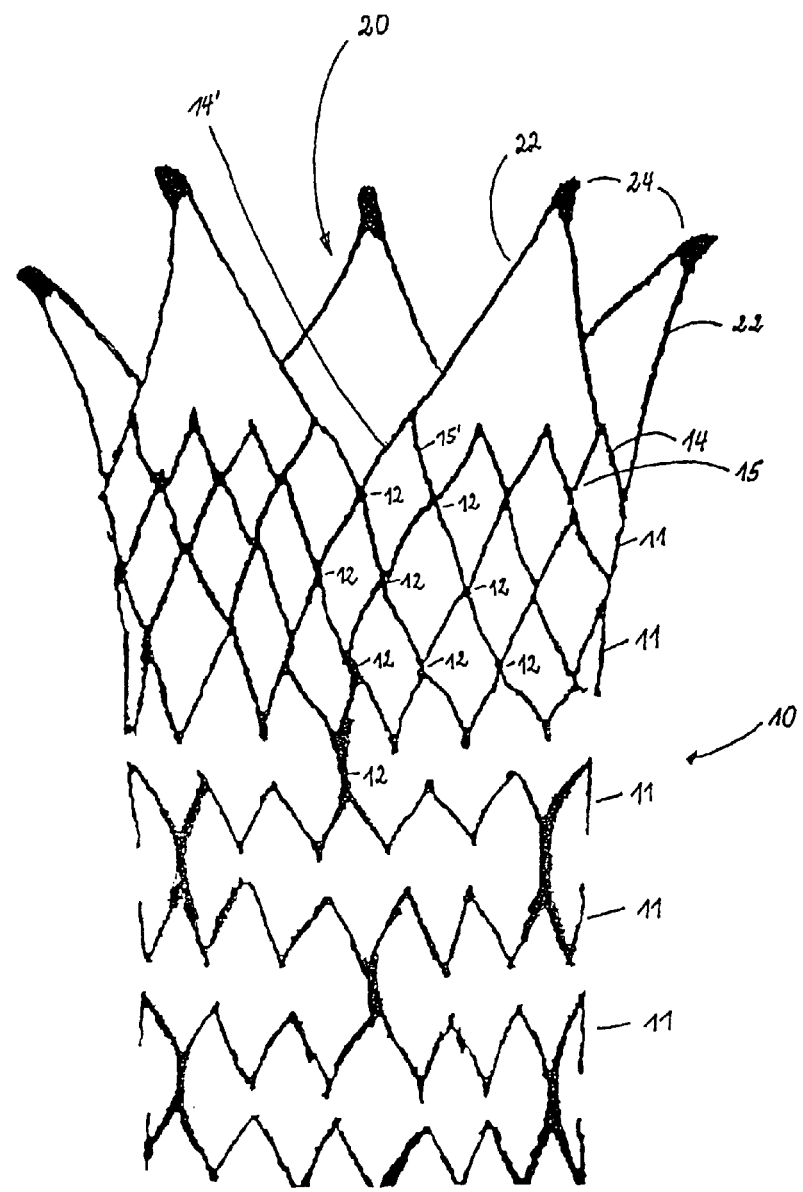
FIG. 3 shows an enlarged partial view of a stent from FIG. 2.

The tubular stent progresses along an axis 26 and is expanded outward at its ends 20, 20'. The end 20 of the stent shown in FIG. 2, enlarged in FIG. 3 for purposes of improved illustration, shows the structure of the wall segments 11, which are constructed of V-shaped wall elements 14, 15, the V-shaped elements being connected to one another at their tips, thereby forming a zigzag line running circumferentially around the stent longitudinal axis 26. The individual wall elements 14, 15 are formed by elastic elements 14 and 15 connected to one another at their frame tip. In the region of the stent end, the successive, annular wall segments 11 are connected to one another at each of their wall elements 14, 15 by means of connecting elements 12, resulting in a rhombic grid network. At the end of this grid network structure, the inventive anchoring elements 22 are arranged in such a way that they are integrally connected with the distal tip of the wall elements 14 and 15. The curved or V-shaped frames of the elements 22 are widened relative to the wall elements 14, 15. This is easily achieved by applying a simply cutting technique during cutting of the stent. The curve tip 24 of the anchoring element 22 is provided with a radiopaque material, so that the position is easily recognizable in the X-ray image by the physician performing the procedure. As can also be deduced from FIGS. 2 and 3, the anchoring elements 22 are bent outward, so that their tips 24 are at a greater distance from the stent axis 26 than the wall and/or elastic elements 14, 15 with which they are connected. It is especially preferred that anchoring elements 22 feature an outwardly directed curvature, with the radius of curvature increasing toward the curve tip. Because the anchoring elements 22 are made of the same elastic material as the stent 10 itself, this shape results in a clamping tension which presses the tips 24 into the surrounding organ, thereby anchoring the entire stent 10.

Figure 4:
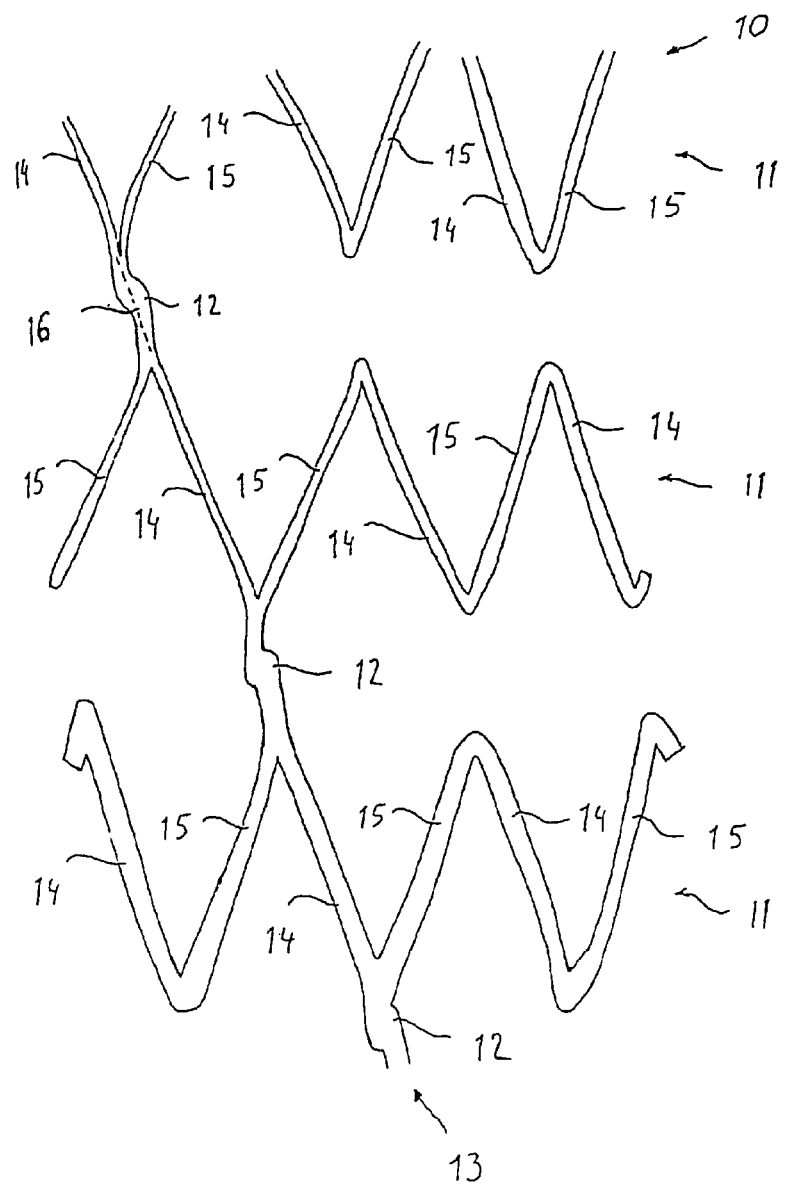
FIG. 4 shows a grid network structure, preferred for the stent according to the invention, as it is used for the central wall region of the stent.

FIG. 4 shows a preferred grid structure, as it is specified in DE-102 43 136, as well as in parallel applications. A stent 10 with this type of pattern is cut, by means of laser beams, from a small tube made of a suitable shape memory material, namely a memory metal such as Nitinol. As the figure indicates, in a first state following the cutting of the pattern in the small tube of memory metal, the first elastic elements 14 and the second elastic elements 15 are arranged adjacent to one another. In the cut, non-expanded state, the first elastic elements 14 and the adjacent second elastic elements 15 are arranged to lie in parallel to one another. The figure clearly shows the roughly s-shaped form of the connecting elements 12. In addition, wall segments 11 arranged to be adjacent to one another are offset relative to one another by an offset corresponding to the thickness of the first elastic elements 14 and the second elastic element 15. In this manner, in a first state a first elastic element 14 of a wall segment 11 is connected at its respective ends by means of connecting elements 12 with a first elastic element 14 of the adjacent wall segments 11, which is offset by the [amount of the] offset. Once the pattern is cut into the tubular blank consisting, for example, of memory metal, the stent produced in this manner is expanded in a second state having a larger diameter than the first state. This second state is then stamped onto the stent 10 in a manner known in the art. For implantation using a catheter, the stent 10 prepared in this manner is then compressed into a state involving a small diameter. Once it is in the desired position, the stent 10 can then be expanded once again into the stamped form by means of the so-called conversion temperature. It is also possible, however, to expand the stent 10 by means of a balloon catheter.

LIST OF REFERENCE NUMBERS

10 Stent
11 Wall segment
12 Connecting element
13 Longitudinal frame
14 First elastic element
15 Second elastic element
16 Direction of application of force
17 Stent
18 Longitudinal frame
20 Tube end
22 Anchoring element
24 Curve tip
26 Tubular axis

What is claimed is:

1. A stent for implantation into a surrounding organ, said stent with a tubular wall formed from a flexible grid structure and progressing around a longitudinal axis, possessing tube ends disposed at opposite axis ends, wherein the wall is comprised of annular wall segments including a terminal annular wall segment, said annular wall segments disposed sequentially along the axis and connected to one another by means of connecting segments, and wherein the annular wall segments comprise wall elements with an elastic structure, characterized in that the wall has, on at least one tube end, a plurality of flexible, anchoring elements said anchoring elements each having two radially curved segments joined at a distal angular pointed tip, and each having a proximal end connected in a single-piece structure directly to an intersection of at least two terminal wall elements and wherein none of the segment ends are directly connected to one another and wherein said anchoring element bridges at least two non-sequential elastic wall elements, said tip, positioned at a larger radial distance from the axis than the terminal wall elements; said anchoring element imparting a pressing force, with said tip, into said surrounding organ, for an anchoring therein, said tip having a radiopaque region, and an annular wall segment in a terminal region of said stent adjacent to said tube end being directly connected to at least one said annular wall segment adjacent thereto at respective intersections of the wall elements in a symmetrical connection without said connecting segments thereby minimizing an expansion of said stent in said terminal region in an axial direction.

2. The stent, as recited in claim 1, wherein the radially curved segments of the anchoring element have a larger material thickness than the wall elements.

3. The stent, as recited in claim 1, wherein it has at least three anchoring elements.

4. The stent, as recited in any one of the preceding claims, wherein the wall elements of the wall segments of the opposite tube end feature radiopaque regions.

5. The stent, as recited in claim 1, 2, or 3, wherein the opposite tube end relative to the tubular axis is radially expanded and has a larger diameter than the center of the stent.

6. The stent, as recited in claim 1, 2, or 3, wherein the expansion along the tubular axis begins at least two annular wall segments before the end.

7. The stent, as recited in claim 1, 2, or 3, wherein at the tube end on at least the terminal wall segment and the wall segment axially disposed in front of it, each wall element of the terminal segment is connected with its element, axially disposed in front of it, of the next segment by means of a connecting segment.

* * * * *